United States Patent [19]

Kozikowski et al.

[11] Patent Number: 4,990,504

[45] Date of Patent: Feb. 5, 1991

[54] AZETIDINE DERIVATIVES TO TREAT MEMORY AND LEARNING DISORDERS

[75] Inventors: Alan P. Kozikowski, Pittsburgh, Pa.; Jarda T. Wroblewski, Kensington; Erminio Costa, Chevy Chase, both of Md.

[73] Assignee: FIDIA-Georgetown Institute for the Neurosciences, Washington, D.C.

[21] Appl. No.: 210,917

[22] Filed: Jun. 24, 1988

Related U.S. Application Data

[63] Continuation-in-part of Ser. No. 74,958, Jul. 1987, Pat. No. 4,946,839

[51] Int. Cl.$^5$ .......................................... A61K 31/395
[52] U.S. Cl. ....................................................... 514/210
[58] Field of Search ........................................ 514/210

[56] References Cited

FOREIGN PATENT DOCUMENTS

| | | |
|---|---|---|
| 29265 | 5/1981 | European Pat. Off. . |
| 169602 | 1/1986 | European Pat. Off. . |
| 221579 | 5/1987 | European Pat. Off. . |
| 318638 | 11/1974 | Fed. Rep. of Germany . |

OTHER PUBLICATIONS

Wasserman et al, Tetrahedron Letters (1984) vol. 25:25, 3111-3114.
Baldwin et al, J. Chem. Soc. Chem. Commun, (1985) pp. 194-196.
Baldwin et al, Tetrahedron Letters (1986) vol. 42:17, 4879-1888.
Wroblewski et al, Proc. Natl. Acad. Sci (1987) vol. 84, pp. 5068-5072.

*Primary Examiner*—Stanley J. Friedman
*Attorney, Agent, or Firm*—Birch, Stewart, Kolasch & Birch

[57] ABSTRACT

This invention relates to novel azetidines and derivatives thereof, as well as to pharmaceutical compositions and methods of treating memory and learning disorders. Another aspect of the invention relates to a method of utilizing the compounds and compositions as biological tools and materials for characterizing excitatory amino acid receptor systems. A further aspect of the invention relates to a method of treating PCP toxicity and abuse.

6 Claims, No Drawings

AZETIDINE DERIVATIVES TO TREAT MEMORY AND LEARNING DISORDERS

This is a continuation-in-part of Ser. No. 07/074,958, filed July 17, 1987, now U.S. Pat. No. 4,946,839.

BACKGROUND OF THE INVENTION

It is known that a selective subtype of excitatory amino acid receptors activated by N-methyl-D-aspartate (NMDA), Glutamate (GLU), and Aspartate (ASP) and competitively inhibited by 2-amino-5-phosphonovaleric acid (APV) are responsible for long term potentiation (LTP). Long term potentiation is defined as the increase in strength of synaptic transmission with repetitive use. LTP has been recognized as one type of synaptic plasticity and is believed to underlie behaviorally significant forms of memory storage and learning. The dysfunctions of excitatory amino acid receptors have been implicated in, e.g., the etiology of senile dementia of the Alzheimer type (SDAT), a disease characterized by severe memory loss, personality changes and symptoms of cortical disconnection; apraxias; asphasias; and agnosias. Glutamate receptors, particularly the NMDA subtype, have been shown to decrease in the neocortex of SDAT patients. The function of this receptor can also be allosterically inhibited by phencyclidine (PCP) and other dissociative anaesthetics, blocking LTP and resulting in learning and memory impairments.

The development of pharmacological agents with the ability to modulate the NMDA receptor in a positive manner has dual importance. In terms of basic neuroscience research it provides the necessary tools for the study of excitatory amino acid receptors, allowing discrimination of the actions of the NMDA receptor subtype from other glutamate receptors. In terms of clinical usefulness, such agents would be useful in treating memory and learning disorders, such as SDAT. The compounds are also effective as therapeutic agents in treating PCP toxicity and abuse.

SUMMARY OF THE INVENTION

This invention relates to novel azetidine dicarboxylic acids, carboxylic acid esters, mono- and diamides, acid alcohols, acid aldehydes, N-benzyl and N-acylated derivatives thereof, as well as to pharmaceutical compositions and methods of treating memory and learning disorders and dysfunctions of excitatory amino acid receptors in mammals, including humans, such as those discussed above. Another aspect of the invention relates to a method of utilizing the compounds and compositions as biological tools and materials for characterizing excitatory amino acid receptor systems. A further aspect of the invention relates to a method of utilizing the compounds and compositions in treating PCP toxicity.

More particularly, the present invention relates to a novel class of azetidine derivatives having the following formula:

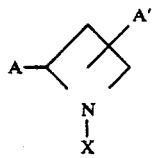

wherein A and A' are the same or different and selected from the group consisting of

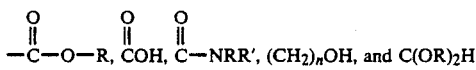

and wherein R and R' are the same or different and selected from the group consisting of hydrogen, lower alkyl, benzyl, and an amino acid; n=1-6; X is hydrogen, an acyl group or a benzyl group; and pharmaceutically acceptable salts thereof.

In the above formula, R and R' can be lower alkyl. Lower alkyl means straight- or branched-chain saturated aliphatic radicals preferably having 1-6 carbon atoms. Exemplary of such lower alkyls are methyl, ethyl, n-propyl, isopropyl, n-butyl, isobutyl, tert-butyl, sec-butyl, n-amyl, n-hexyl and the like. The preferred group of lower alkyl radicals are straight and branched chain $C_1$–$C_4$ alkyl radicals.

X in formula (I) is a benzyl group or hydrogen or an acyl group, especially lower acyl or $C_{1-6}$ acyl, and may particularly be formyl, acetyl, propionyl and butyoyl. Particularly preferred of the N-acyl derivatives is the N-acetyl derivative wherein X is acetyl.

The azetidine derivatives of the present invention can be 2,3- or 2,4-disubstituted azetidines, preferably 2,4-disubstituted azetidines.

The azetidine derivatives of the present invention exhibit stereoselectivity in their biological action. The cis-isomers have particularly been found to be the most biologically active.

The preferred compounds of the invention are $C_1$–$C_4$ straight or branched chain cis-2,4-disubstituted azetidine derivatives and their nontoxic, pharmaceutically acceptable salts.

Exemplary of such compounds are cis-azetidine-2,4-dicarboxylic acid dimethyl ester; cis-azetidine-2,4-diocarboxylic acid t-butyl methyl ester; cis-acetidine-2,4-dicarboxylic acid mono t-butyl ester; cis-azetidine-2,4-dicarboxylic acid; cis-azetidine-2,4-dicarboxylic acid di-t-butyl ester; cis-N-acetylazetidine-2,4-dicarboxylic acid; N-(cis-4-carboxyazetidine-2-carbonyl)glycine; cis-4-carbamoylazetidine-2-carboxylic acid; cis-azetidine-2,4-dicarboxamide; cis-azetidine-2,3-dicarboxylic acid; cis-azetidine-2,3-dicarboxamide; cis-4-(hydroxymethyl)azetidine-2-carboxylic acid; cis-4-(dimethoxymethyl)azetidine-2-carboxylic acid.

The cis-azetidine derivatives of the present invention include pharmaceutically acceptable salts of the compounds of the present invention. Exemplary of such salts are the oxalate, citrate, tartrate, hydrochloride salts, and the like.

The invention also relates to the process of preparing the aforementioned azetidine derivatives. In defining the processes, a lower alkyl group is defined as being $C_1$–$C_6$, straight or branched chain radicals.

Stoichiometric amount is defined as the amount of reactant needed to react with an equivalent of another reactant. For example, when preparing a 2,4-azetidine dicarboxylic acid mono substituted ester, one would use ½ of a stoichiometric amount of the reactant lower alcohol.

Solvents for running the reaction are any organic solvents. Particularly preferred solvents include carbon tetrachloride, benzene, acetone, toluene, methanol, dioxane, tetrahydrofuran, diethyl ether, hexane, and ethyl acetate. In terms of temperature ranges for running the reactions, −10° C. to 100° C. are preferred.

More particularly the invention is directed to a process for preparing azetidine-2,4-dicarboxylic acids and their (di)esters comprising (a) reacting

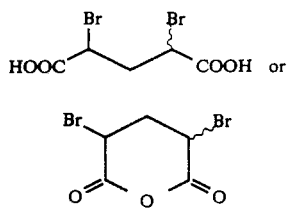

with benzyl alcohol, a lower alcohol, or benzyl alcohol and a lower alcohol to produce a compound of the formula

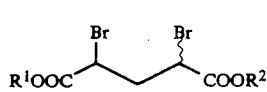

wherein $R^1$ and $R^2$ are the same or different and represent benzyl or a lower alkyl;

(b) reacting said compound of formula (III) with benzylamine to form

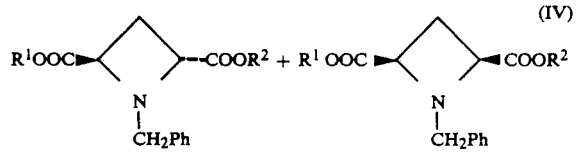

wherein $R^1$ and $R^2$ are defined as above and Ph is a phenyl group;

(c) separating cis- and trans-isomers of said compound of formula IV; and (d) subjecting either of said isomers to N-debenzylation to form, respectively,

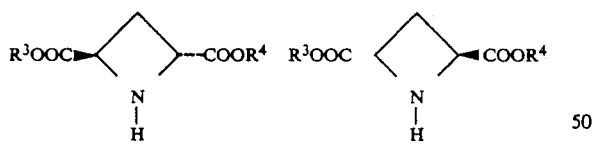

where $R^3$ and $R^4$ are H and/or lower alkyl.

Moreover, a preferred embodiment of preparing azetidine-2,4-dicarboxylic acid (di)esters is wherein the lower alcohol is selected from the group consisting of $C_1$-$C_6$, straight or branched chain alcohols.

This invention also relates to a process for preparing azetidine-2,3 dicarboxylic acids comprising (a) irradiating a compound of the formula

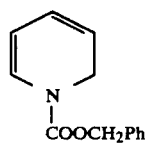

wherein Ph is a phenyl group, to produce a compound of the formula

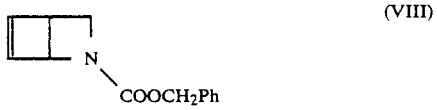

(b) reacting a compound of formula VIII with ozone followed by oxidative workup to produce a compound of the formula

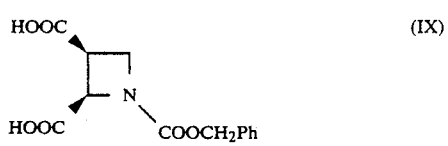

(c) subjecting the compound of formula IX to N-deacylation to form

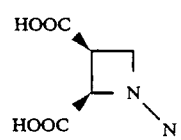

A further aspect of the present invention is directed to a process for preparing azetidine-2,3-dicarboxylic acid diesters comprising (a) irradiating a compound of formula

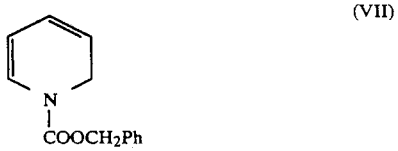

wherein Ph is a phenyl group, to produce a compound of formula

(b) reacting a compound of formula VIII with ozone followed by oxidative workup to produce a compound of formula

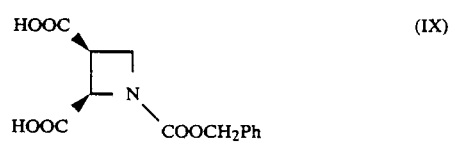

(c) esterifying the compound of formula VIII by reacting said compound with a lower alcohol, or benzyl alcohol and a lower alcohol, to produce a compound of formula

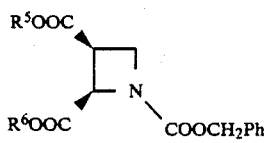

(X)

wherein $R^5$ and $R^6$ are lower alkyl or benzyl; and (d) subjecting said compound of the formula X to N-deacylation to form

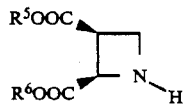

wherein $R^5$ and $R^6$ are H and/or lower alkyl.

Still, a further aspect of the invention is directed to a process for preparing azetidine-2,3-dicarboxamides comprising:

(a) reacting a compound of formula IX

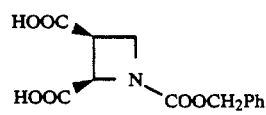

(IX)

wherein Ph is a phenyl group with an amine having the formula

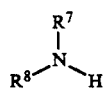

wherein $R^7$ and $R^8$ are each H, or lower alkyl, to form the compound

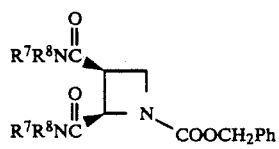

(XI)

(b) subjecting said compound XI to N-deacylation to form

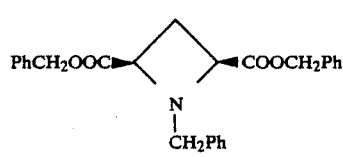

This invention also relates to a process for preparing azetidine-2,4-(di)carboxamides comprising:

(a) reacting XII

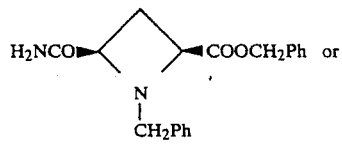

(XII)

wherein Ph is a phenyl group, with a stoichiometric amount $MeAl(Cl)NH_2$ to form compounds of the formula

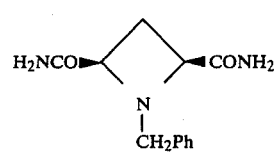

(XIII)

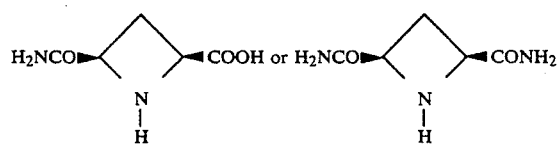

(XIV)

(b) subjecting either of said XIII or XIV to N-debenzylation to form, respectively

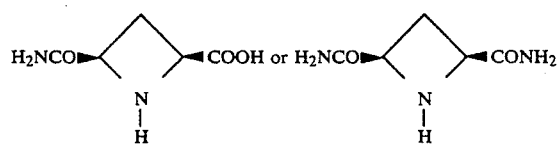

This invention also relates to a process for preparing cis-4-(hydroxy-methyl)azetidine-2-carboxylic acid which comprises (a) reacting a compound

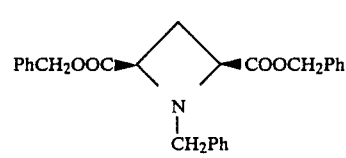

(XV)

wherein Ph is a phenyl group, with $Me_2AlSeMe$ to form a compound of the formula

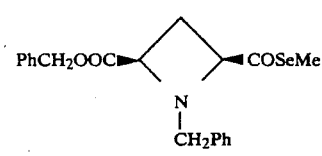

(XX)

(b) reacting a compound of formula XX with a reducing agent to form a compound

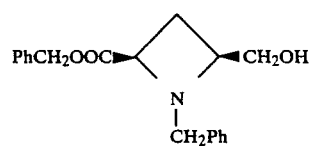

(XXI)

(c) subjecting the compound of formula XXI to N-debenzylation to form the compound

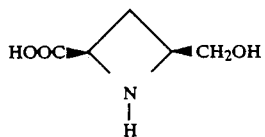 (XXII)

A process for preparing cis-4-(hydroxy-alkyl)azetidine-2,carboxylic acid which comprises
(a) reacting a compound of the formula

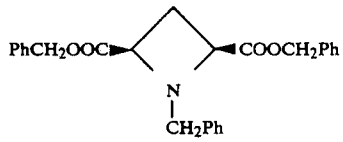 (XV)

wherein Ph is a phenyl group, sequentially with a reducing agent in a lower alcohol solvent, and then with an acid to form the compound

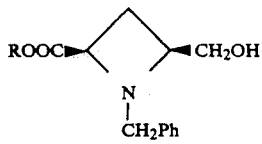 (XXIII)

wherein R is a lower alkyl group.

A process of preparing cis-4-(dialkoxymethyl)azetidine-2-carboxylic acid which comprises
(a) reacting a compound of formula

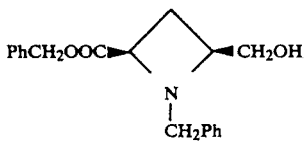 (XXI)

wherein Ph is a phenyl group, first with (COCl)$_2$ and DMSO, and then triethylamine, to form a compound of the formula

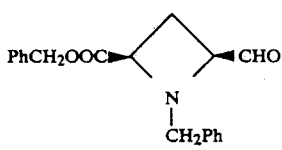 (XXIV)

(b) reacting compound XXIV and a lower alcohol to form compound

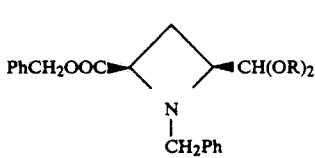 (XXV)

wherein R is a lower alkyl group
(c) subjecting the compound of formula XXV to N-debenzylation to form

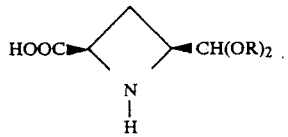 (XXVI)

wherein R is a lower alkyl group.

The invention also relates to compositions of the compounds of formula I for carrying out the aforementioned methods of treatment in mammals, including humans, as well as for carrying out the biological tools and materials for characterizing excitatory amino acid receptor systems.

DETAILED DESCRIPTION OF THE INVENTION

The following examples further illustrate the present invention and will enable others skilled in the art to understand it more completely. It is to be understood, however, that the invention is not limited solely to the particular examples below. All percentages are by weight, unless otherwise specified.

MODE OF PREPARATION

The following examples explain in greater detail the preparation of the intermediates and the final products of the present invention.

General Procedures

All reactions, if not described otherwise, are run under an ordinary atmosphere with exclusion of moisture. Column chromatography is performed on Merck No. 7734 Kieselgel 60 (0.063–0.200 mm) with ethyl acetate/hexanes as eluent if not stated otherwise. $^1$H NMR spectra are recorded on a Bruker AF 300 instrument at 300 MHz in CDCl$_3$ or D$_2$O using TMS or sodium 3-trimethylsilyl-propanesulfonate as internal standards. Coupling constants are given in Hz; they are evaluated by first-order rules with an estimated accuracy of 0.5 Hz. IR spectra are measured on liquid film samples, KBr pellets, or nujol suspensions on an IBM IR/32 FTIR spectrometer. Mass spectra were recorded on Varian CH 5 and VG 70-G instruments. Elemental analyses were carried out by Galbraith Laboratories, Inc., Knoxville, Tennessee. Melting points were determined on a Thomas Hoover capillary melting point apparatus and are uncorrected.

Cis- and trans-azetidine carboxylic derivatives are prepared by brominating glutaric anhydride in the presence of a catalyst to form 2,4-dibromoglutaric acid. Depending on the product desired, as will be explained in greater detail hereinbelow, the 2,4-dibromoglutaric acid can be further reacted with acetyl chloride to form 2,4-dibromoglutaric anhydride.

These two intermediates can then be reacted with a variety of alcohols to arrive at the compounds of the present invention.

EXAMPLE 1

Preparation of 2,4-Dibromoglutaric acid

The preparation is conducted in a well-ventilated hood because toxic fumes (Br$_2$, HBr, CO) evolve. A 50 ml 3-necked flask equipped with thermometer, dropping funnel (its stem extending under the surface of the liquid by means of a piece of teflon tubing), reflux condenser and magnetic stirrer is charged with 10.1 g (88.5 mmol) of glutaric anhydride (Aldrich) and 136 mg (4.4 mmol) of red phosphorus (Aldrich), and heated in an oil bath to an inner temperature of approx. 100° C. 9.9 ml (195 mmol) of bromine is added dropwise with stirring within 1 hour at a temperature of 105°–110° C., and the mixture is stirred for another 2 hours at 110°–115° C. (HBr evolution has become very slow at this point). After cooling to 50° C., the viscous product is poured into 7.1 ml (180 mmol) of 95–97% formic acid, whereon vigorous gas (presumably CO) evolution takes place. After standing overnight, the solid is recrystallized from ether/chloroform (2 crops) and chloroform (another 2 crops), yielding a total of 11.3 g (44%) of a tan product.

EXAMPLE 2

Preparation of 2,4-Dibromoglutaric anhydride 10.0 g (34.5 mmol) of 2,4-dibromoglutaric acid and 4.9 ml (69 mmol) of acetyl chloride are refluxed for a period of 2 hours. Volatiles are removed at 10 torr up to 90° C., and the residue bulb-to-bulb distilled (75°–90° C./0.25 torr), yielding 8.9 g (95%) of a colourless, viscous oil. $^1$H NMR (CDCl$_3$): dl isomer: δ 4.90 (t, 2H, J=6), 2.87 (t, 2H, J=6); meso isomer: 4.77 (dd, 2H, J=6, 10), 3.15 (dt, 1H, J=6 (t), 15 (d)), approx. 2.85 (1H, partially overlapping); dl/meso=5:1. IR (neat): 3007, 2942, 1817, 1775, 1439, 1242, 1109, 1038, 972, 932, 847, 691, 617 cm$^{-1}$.

EXAMPLE 3

Preparation of cis-Azetidine-2,4-dicarboxylic acid dimethyl ester 1.14 g (3.93 mmol) of 2,4-dibromoglutaric acid, 1 ml of methanol, 1.2 ml of CCl$_4$, and 1 drop of conc. sulfuric acid are refluxed for 8 hours. Aqueous workup (CH$_2$Cl$_2$/sat. NaHCO$_3$), filtration over silica gel, and evaporation yields 0.87 g (70%) of dimethyl 2,4-dibromoglutarate. $^1$H NMR (CDCl$_3$): δ3.82 (s, 6H); dl isomer: δ4.53 (dd, 2H, J=6.5, 8), 2.68 (dd, 2H, J=6.5, 8); meso isomer: δ4.41 (t, 2H, J=7.5), 2.89 (dt, 1H, J=7.5 (t), 14.5 (d)), 2.64 (dt, 1H, J=7.5 (t), 14.5 (d)); dl/meso=3:1.IR (neat): 3004, 2955, 1740, 1437, 1300, 1267, 1215, 1156, 851 cm$^{-1}$.

Dimethyl 2,4-dibromoglutarate (1.98 mmol), 3 molar equivalents of benzylamine, and enough DMF to prepare an approx. 0.12M solution of dimethyl-2,4-dibromoglutarate are stirred at 80° C. for 2 hours. The solvent is distilled into a cold trap at 0.2–0.3 torr/40° C. bath temperature, the residue taken up in CH$_2$Cl$_2$, and the solution washed with saturated aq. NaHCO$_3$. After drying over MgSO$_4$ and evaporation, the residue is chromatographed using a silica gel column to yield, after a forerun, first the trans, then the cis-isomer of N-benzylazetidine-2,4-dicarboxylic acid dimethyl ester as amber, viscous oils.

trans isomer 36% yield. $^1$H NMR (CDCl$_3$): δ 7.3–7.2 (m, 5H), 4.22 (t, 2H, J=7), 3.87 (narrow AB system, 2H, J=13.5), 3.65 (s, 6H), 2.51 (t, 2H, J=7).
IR (neat): 2953, 1736, 1437, 1354, 1200, 1030, 749, 698 cm$^{-1}$.

cis isomer 32% yield. $^1$H NMR (CDCl$_3$): δ 7.37–7.22 (m, 5H), 3.88 (s, 2H), 3.64 (s, 6H), 3.63 (t, 2H, J=8.5), 2.50 (dt, 1H, J=8.5 (t), 10.5 (d)), 2.34 (dt, 1H, J=8 (t), 10.5 (d)). IR (neat): 2953, 1744, 1437, 1225, 1202, 1042, 700 cm$^{-1}$.

79 mg (0.3 mmol) of cis-N-benzylazetidine-2,4-dicarboxylic acid dimethyl ester and 25 mg of Pd(OH)$_2$ (20% on C, 31% H$_2$O, Aldrich) in 10 ml of methanol are hydrogenated under 3 atm of hydrogen in a Parr shaker for 6 hours. The catalyst is filtered off and thoroughly washed, the solution evaporated, and the residue filtered over a short column to yield 23.4 mg (45%) of cis-azetidine-2,4-dicarboxylic acid dimethyl ester. $^1$H NMR (CDCl$_3$): δ4.27 (dd, 2H, J=6.5, 8.5), 3.76 (s, 6H), 2.95 (dt, 1H, J=8.5 (t), 12 (d)), 2.60 (dt, 1H, J=6.5 (t), 12 (d)). IR (neat): 3345, 2955, 1740, 1437, 1231, 1042 cm$^{-1}$. Mass spectrum: m/z 173 (7%), 114 (100), 82 (44), 59 (14), 55 (32), 54 (98). Calcd. for C$_7$H$_{11}$NO$_4$: 173.0688, found: 173.0688.

EXAMPLE 4

Preparation of trans- and cis-Azetidine-2,4-dicarboxylic acid t-butyl methyl ester 544 mg (2 mmol) Of 2,4-dibromoglutaric anhydride, 0.5 ml of CH$_2$Cl$_2$, and 85 μl (2.1 mmol) of methanol are stirred in a capped vial at room temperature for 5.5 hours, after which time the IR spectrum indicates the absence of starting materials. 5 ml of benzene and 10 μl of DMF are added, the solution is then cooled in an ice bath, and 0.19 ml (2.2 mmol) of oxalyl chloride in 2 ml of benzene are added dropwise. Stirring is continued for 15 min. at 0° C. and for 45 min. at room temperature, after which time gas evolution (HCl, CO, CO$_2$) virtually ceases. Volatiles are evaporated in vacuo, and the residue is taken up in 2 ml of CH$_2$Cl$_2$. This solution is added dropwise with ice cooling to a solution of 0.47 ml(5 mmol) of tert.-butanol, 0.35 ml (2.5 mmol) of triethylamine, and 12.2 mg (0.1 mmol) of 4-dimethylaminopyridine in 3 ml of CH$_2$Cl$_2$. After stirring at 0° C. and room temperature for 20 min. each, the mixture is washed with aqueous KHSO$_4$ solution, dried over MgSO$_4$, evaporated, and filtered over silica gel to afford 410 mg (57%) of t-butyl methyl 2,4-dibromoglutarate. $^1$H NMR (CDCl$_3$): δ4.52, 4.41, 4.40, 4.27 (each t, $^1$H, J=7.5), 3.81 (s, 3H), 1.49 (s,9H); dl isomer: δ2.61 (t, 2H, J=7.5); meso isomer: δ 2.83 (dt, 1H, J=7.5 (t), 15 (d)), 2.58 (dt, 1H, J=7.5 (t), 15 (d)); dl/meso=2:1. IR (neat): 2980, 1742, 1437, 1370, 1277, 1150, 843 cm$^{-1}$.

t-Butyl methyl 2,4-dibromoglutarate (1.08 mmol), 3 molar equivalents of benzylamine, and enough DMF to prepare an approx. 0.12M solution of t-butyl methyl 2,4-dibromoglutarate are stirred at 80° C. for 2 hours. The solvent is distilled into a cold trap at 0.2–0.3 torr/40° C. bath temperature, the residue taken up in CH$_2$Cl$_2$, and the solution washed with saturated aq. NaHCO$_3$. After drying over MgSO$_4$ and evaporation, the residue is chromatographed using silica gel to yield, after a forerun, first the trans isomer, then the cis-isomer of N-benzylazetidine-2,4-dicarboxylic acid t-butyl methyl ester as amber, viscous oils.

trans isomer 32% yield . $^1$H NMR (CDCl$_3$): δ 7.35–7.2 (m, 5H), 4.20 (t, 1H, J=7), 4.09 (t, 1H, J=6.5), 3.89 (s, 2H), 3.64 (s, 3H), 2.46 (dd, 2H, J=6.5, 7), 1.42 (s, 9H). IR (neat): 2977, 1734, 1455, 1368, 1237, 1202, 1156, 1028, 745, 700 cm$^{-1}$.

cis isomer: 30% yield. $^1$H NMR (CDCl$_3$): δ 7.35–7.2 (m, 5H), 3.86 (narrow AB system, 2H, J=13.5), 3.63 (s, 3H), 3.57 (t, $^1$H, J=8.5), 3.49 (t, 1H, J=8.5), 2.44 (dt, 1H, J=8.5 (t), 10.5 (d)), 2.29 (dt, 1H, J=8 (t), 10.5 (d)), 1.37 (s, 9H). IR (neat): 2977, 1738, 1455, 1368, 1229, 1157, 1030, 847, 754, 708 cm$^{-1}$.

The trans- and cis-azetidine-2,4-dicarboxylic acid t-butyl methyl esters are obtained in the same way as in example 3 from their respective stereo-chemically pure N-benzyl precursors.

cis-isomer in 48% yield. $^1$H NMR (CDCl$_3$): δ4.21 (dd, 1H, J=6, 9), 4.10 (dd, 1H, J=6, 9), 3.76 (s, 3H), 3.12 (br. s., 1H), 2.96 (dt, 1H, J=9 (t), 12 (d)), 2.49 (dt, 1H, J=6 (t), 12 (d)), 1.48 (s, 9H). IR (neat): 3276, 2975, 1728, 1370, 1269, 1159, 1100, 1088, 1026, 833, 776, 764 cm$^{-1}$.

trans-isomer in 59% yield. $^1$H NMR (CDCl$_3$): δ4.35 (dd, 1H, J=6.5, 9), 4.13 (dd, 1H, J=5.5, 9), 3.77 (s, 3H), 2.81 (br. s., 1H), 2.72 (ddd, 1H, J=6.5, 9, 11.5), 2.60 (ddd, 1H, J=5.5, 9, 11.5), 1.49 (s, 9H). IR (neat): 3328, 2979, 1732, 1370, 1237, 1159, 1059, 845 cm$^{-1}$.

EXAMPLE 5

Preparation of trans- and cis-Azetidine-2,4-dicarboxylic acid mono t-butyl ester 2.18 g (8 mmol) of 2,4-dibromoglutaric anhydride, 0.83 ml (8 mmol) of benzyl alcohol, and 2 ml of chloroform are stirred for 1 hour at room temperature and for another hour under reflux. 20 ml of benzene and 0.1 ml of DMF are added, the solution is cooled in an ice bath, and 1.05 ml (12 mmol) of oxalyl chloride in 5 ml of benzene is added dropwise. Stirring is continued for 40 min. at 0° C. and 70 min. at room temperature, after which time gas evolution has virtually ceased. Volatiles are evaporated in vacuo, and the residue is taken up in 5 ml of CH$_2$Cl$_2$. This solution is added dropwise with ice cooling to a solution of 1.4 ml (15 mmol) of tert.-butanol, 1.4 ml (10 mmol) of triethylamine, and 19.5 mg (0.16 mmol) of 4-dimethylaminopyridine in 15 ml of CH$_2$Cl$_2$. After stirring at 0° C. and room temperature for 20 min. each, the mixture is washed with aqueous KHSO$_4$ solution, dried over MgSO$_4$, evaporated, and filtered over silica gel to afford 2.65 g (76%) of benzyl t-butyl 2,4-dibromoglutarate. $^1$H NMR (CDCl$_3$): δ7.37 (br. s., 5H), 5.22 (2 narrow AB systems, 2H), 1.48 (s, 9H); dl isomer: δ4.54 (t, 1H, J=7.5), 4.39 (t, 1H, J=7.5), 2.63 (t, 2H, J=7.5); meso isomer: δ4.44 (t, 1H, J=7.5), 4.26 (t, 1H, J=7.5), 2.83 (dt, 1H, J=7.5 (t), 15 (d)), 2.59 (dt, 1H, J=7.5 (t), 15 (d)); dl/meso=1:2. IR (neat): 2980, 1736, 1456, 1370, 1266, 1148, 843, 752, 696 cm$^{-1}$.

Benzyl t-butyl 2,4-dibromoglutarate (2.13 mmol), 3 molar equivalents of benzylamine, and enough DMF to prepare an approx. 0.12M solution of benzyl t-butyl 2,4-dibromoglutarate are stirred at 80° C. for 2 hours.

The solvent is distilled into a cold trap at 0.2-0.3 torr/40° C. bath temperature, the residue taken up in CH$_2$Cl$_2$, and the solution washed with saturated aq. NaHCO$_3$. After drying over MgSO$_4$ and evaporation, the residue is chromatographed using a silica gel column to yield—after a forerun—first the trans isomer, then the cis-isomer of N-benzylazetidine-2,4-dicarboxylic acid benzyl t-butyl ester as amber, viscous oils.

cis isomer: 33% yield. $^1$H NMR (CDCl$_3$): δ 7.38–7.18 (m, 10H), 5.10, 5.03 (AB system, 2H, J=12.5), 3.88, 3.84 (AB system, 2H, J=13), 3.61 (t, 1H, J=8), 3.46 (t, 1H, J=8), 2.48 (dt, 1H, J=8 (t), 11.5 (d)), 2.28 (dt, 1H, J=8 (t), 11.5 (d)), 1.36 (s, 9H). IR (neat): 2979, 1738, 1455, 1368, 1229, 1159, 1028, 845, 745, 698 cm$^{-1}$.

267 mg (0.7 mmol) of stereochemically pure trans or cis-N-benzylazetidine-2,4-dicarboxylic acid benzyl t-butyl ester, 50mg of 10% Pd/C, and 20 ml of methanol are hydrogenated under 3 atm of hydrogen in a Parr shaker for 4 hours. The catalyst is filtered off and thoroughly washed, and the solution evaporated to dryness and dried in vacuo to afford as off-white solids the trans- or cis-azetidine-2,4-dicarboxylic acid mono-t-butyl ester.

cis isomer in 94% yield. $^1$H NMR (D$_2$O): δ4.98 (dd, 1H, J=8, 10), 4.75 (dd, 1H, J=8, 10), 3.15 (dt, 1H, J=10 (t), 12.5 (d)), 2.57 (dt, 1H, J=8 (t), 12.5 (d)), 1.51 (s, 9H). IR (KBr): 3434, 2998, 1738, 1617, 1563, 1385, 1368, 1248, 1161, 843 cm$^{-1}$. Mass spectrum: m/z 100 (100%), 82 (33), 57 (81), 56 (20), 55 (17), 54 (37), 41 (39).

trans isomer in 92% yield. $^1$H NMR (D$_2$O): δ4.91 (dd, 1H, J=7, 10), 4.71 (dd, 1H, J=7.5, 10), 2.98–2.77 (m, 2H), 1.52 (s, 9H). IR (KBr): 3438, 2982, 1740, 1632, 1570, 1389, 1281, 1248, 1175, 1080, 779, 515 cm$^{-1}$.

EXAMPLE 6

Preparation of trans- and cis-Azetidine-2,4-dicarboxylic acid 2.18 g (8 mmol) of 2,4-dibromoglutaric anhydride, 2.1 ml (20 mmol) of benzyl alcohol, and 2 ml of benzene are stirred for 1.5 hours at room temperature. 76 mg (0.4 mmol) of p-toluenesulfonic acid monohydrate and 8 ml of benzene are added, and the solution is refluxed under a Dean-Stark trap for 2 hours. Filtration over silica gel and evaporation yields 3.77 g (100%) of dibenzyl 2,4-dibromoglutarate as a colourless oil. $^1$H NMR (CDl$_3$): δ7.37 (br. s., 10H), 5.21 (narrow AB system, 4H, J=12.5); dl isomer: δ4.55 (dd, 2H, J=6.5, 7.5), 2.69 (dd, 2H, J=6.5, 7.5); meso isomer: δ4.42 (t, 2H, J=7.5), 2.90 (dt, 1H, J=7.5 (t), 14.5 (d)), 2.66 (dt, 1H, J=7.5 (t), 14.5 (d)); dl/meso=6:1. IR (neat): 3034, 1740, 1499, 1456, 1385, 1273, 1154, 750, 696 cm$^{-1}$.

Dibenzyl-2,4-dibromoglutarate (7.93 mmol), 3 molar equivalents of benzylamine, and enough DMF to prepare an approx. 0.12M solution are stirred at 80° C. for 2 hours. The solvent is distilled into a cold trap at 0.2-0.3 torr/40° C. bath temperature, the residue taken up in CH$_2$Cl$_2$, and the solution washed with saturated aq. NaHCO$_3$. After drying over MgSO$_4$ and evaporation, the residue is chromatographed using a column to yield—after a forerun—first the trans, then the cis-isomer of N-benzylazetidine-2,4-dicarboxylic acid dibenzyl ester as amber, viscous oils.

trans isomer: 38% yield. $^1$H NMR (CDCl$_3$): δ 7.4–7.15 (m, 15H), 5.09 (narrow AB system, 4H), 4.25 (t, 2H, J=7), 3.89, 3.85 (AB system, 2H, J=13), 2.52 (t, 2H, J=7). IR (neat): 3033, 2953, 1732, 1497, 1455, 1345, 1171, 1028, 737, 698 cm$^{-1}$.

cis isomer: 27% yield. $^1$H NMR (CDCl$_3$): δ 7.4–7.2 (m, 15H), 5.12, 5.04 (AB system, 4H,J=12.5), 3.91 (s, 2H), 3.68 (t, 2H, J=8), 2.58 (dt, 1H, J=8.5 (t), 10.5 (d)), 2.38 (dt, 1H, J=8 (t), 10.5 (d)). IR (neat): 3033, 1744, 1497, 1455, 1173, 1028, 911, 735, 696 cm$^{-1}$.

208 mg (0.5 mmol) of stereochemically pure trans or cis-N-benzylazetidine-2,4-dicarboxylic acid dibenzyl ester and 20 mg of 10% Pd/C in 15 ml of methanol are hydrogenated as above. The reaction mixture is diluted with 50 ml of warm water, filtered, and evaporated to dryness to afford as off-white solids the trans- or cis azetidine-2,4-dicarboxylic acid in virtually quantitative yield.

cis isomer: $^1$H NMR (D2O): δ4.87 (dd, 2H, J=8, 10), 3.19 (dt, 1H, J=10 (t), 12 (d)), 2.60 (dt, 1H, J=8 (t), 12 (d)). IR (KBr): 3443, 3158, 1727, 1630, 1563, 1404, 1246, 843, 779, 604, 542 cm$^{-1}$. Elemental analysis: calcd. C 41.38, H 4.86, N 9.65, found: C 41.25, H 4.80, N 9.52. IR (nujol suspension): 3158, 2684, 2624, 2575, 2408, 1732, 1657, 1563, 1404, 1379, 1246, 1161, 1044, 1033, 978, 891, 868, 843, 779, 752, 727, 604 cm$^{-1}$.

trans isomer $^1$H NMR (D$_2$O): δ2.88 (t, J=8.5); another signal is hidden under the HDO signal (approx. 4.77). In D$_2$O/DCl: 5.12 (t, 2H, J=8.5), 3.08 (t, 2H, J=8.5). IR (KBr): 3426, 3013, 1744, 1628, 1406, 1260, 997, 808, 776 cm$^{-1}$.

EXAMPLE 7

Preparation of cis-Azetidine-2,4-dicarboxylic acid di-tert.butyl ester

To 1.45 g (5 mmol) of 2,4-dibromoglutaric acid in 1.5 ml of ether is added at −78° C. 1.5 ml of liquefied isobutene, followed by 3 drops of conc. sulfuric acid. The solution is stirred at room temperature in a screw-capped vial (slight pressure formation; use adequate shielding) for 22 h, cooled, and poured into a mixture of saturated aq. NaHCO$_3$ and ether. The organic phase is dried over MgSO$_4$ and chromatographed on SiO$_2$ (ethyl acetate (EtOAc)/hexanes 1:5). Following impure di-tert.butyl ester, two side products are eluted. The crude 2,4-dibromoglutaric acid di-tert.butyl ester is again chromatographed on SiO$_2$ (EtOAc/hexanes 1:5) to remove slightly more polar minor impurities, resulting in 0.97 g (48%) of a colorless oil. $^1$H NMR (CDCl$_3$): dl isomer: δ4.38 (dd, 2H, J=6.5, 8) 2.56 (dd, 2H, J=6.5, 8); meso isomer: δ4.28 (t, 2H, J=7.5), 2.77 (dt, 1H, J=15 (d), 7 (t)), 2.55 (dt, 1H, J=14.5 (d), 7.5 (t)); both δ1.49 (s, 18H). dl/meso=1:2. IR (neat): 2980, 2934, 1733, 1478, 1458, 1424, 1395, 1370, 1302, 1260, 1223, 1146, 1036, 969, 843, 761 cm$^{-1}$.

cis-N-Benzylazetidine-2,4-dicarboxylic acid di-tert.butyl ester is obtained by warming 958 mg (2.38 mmol) of 2,4-dibromoglutaric acid di-tert.butyl ester and 0.79 ml (7.2 mmol) of benzylamine in 18 ml of DMF to 80° C. for 4 h.

The solvent is distilled into a cold trap at 0.2–0.3 torr/40° C. bath temp., the residue taken up in CH$_2$Cl$_2$, and the solution washed with saturated aq. NaHCO$_3$. After drying over MgSO$_4$ and evaporation, the residue is chromatographed using a silica gel column to yield, after a forerun, first the trans, and then the cis isomer of N-benzylazetidine-2,4-dicarboxylic acid di-tert.butyl ester.

trans isomer: 295 mg (36%). mp. 46°–48° C. $^1$H NMR (CDCl$_3$): δ7.34–7.18 (m, 5H), 4.07 (t, 2H, J=7), 3.95, 3.88 (AB system, 2H, J=13), 2.41 (t, 2H, J= 7), 1.41 (s, 18H). IR (neat): 3064, 3030, 2978, 2933, 1726, 1495, 1480, 1455, 1393, 1368, 1239, 1154, 1021, 983, 912, 840, 735, 700 cm$^{-1}$.

cis isomer: 316 mg (38%). mp. 53°–56° C. $^1$H NMR (CDCl$_3$): δ7.34–7.19 (m, 5H), 3.84 (s, 2H), 3.44 (t, 2H, J=8), 2.39 (dt, 1H, J=11 (d), 8.5 (t)), 2.23 (dt, 1H, J=10.5 (d), 8 (t)), 1.37 (s, 18H). IR (neat): 3063, 2978, 2932, 1735, 1495, 1479, 1455, 1393, 1368, 1233, 1156, 1061, 1019, 994, 915, 845, 737, 705 cm$^{-1}$.

307 mg (884 μmol) of cis-N-benzylazetidine-2,4-dicarboxylic acid di-tert.butyl ester in 25 ml of methanol is hydrogenated in a Parr shaker over 100 mg of 20% Pd(OH)$_2$/C (containing 31% water) under 4 atm of hydrogen for 7.5 h. The catalyst is filtered off through a double paper filter and thoroughly washed with methanol. Evaporation and filtration over SiO$_2$ (EtOAc/hexanes 1:1) affords 149 mg (66%) of cis-azetidine-2,4-dicarboxylic acid di-tert.butyl ester as a yellowish oil which solidifies spontaneously. mp. 47°–48.5° C. $^1$H NMR (CDCl$_3$): δ4.04 (dd, 2H, J=5.5, 9), 3.2 (br., 1H), 2.97 (dt, 1H, J=12 (d), 9 (t)), 2.38 (dt, 1H, J=12 (d), 5.5 (t)), 1.48 (s, 18H). IR (neat): 3328, 2979, 2934, 1731, 1480, 1458, 1394, 1369, 1280, 1257, 1156, 1103, 1048, 1031, 892, 846, 734 cm$^{-1}$.

EXAMPLE 8

Preparation of cis-N-Acetylazetidine-2,4-dicarboxylic acid

To 29.2 mg (0.2 mmol) of cis-azetidine-2,4-dicarboxylic acid and 65 μl (0.8 mmol) of pyridine in 0.5 ml of water is added with stirring in several portions within 1.5h 150 μl (1.6 mmol) of acetic anhydride. After 3.5 h at room temperature, the mixture is filtered over a short column of Dowex ® 50W-X8 resin (H+ form, washed with 10% HCl and distilled water before use) to remove pyridine (elution with water). The crude material obtained after evaporation is chromatographed on SiO$_2$ (isopropanol/water/acetic acid 14:5:1) and evaporated. The product holds acetic acid tenaciously; after drying at 100° C. (0.1 torr, overnight), 35.5 mg of an amber glass is obtained which still contains 4% of acetic acid (corrected yield: 91%). $^1$H NMR (D$_2$0): δ5.06 (dd, 2H, J=5.5, 10), 3.07 (dt, 1H, J=12(d), 10 (t)), 2.43 (dt, 1H, J=12(d), 5.5(t)), 1.96 (s,3H).

EXAMPLE 9

Preparation of N-(cis-4-Carboxyazetidine-2-carbonyl)glycine

To 80.5 mg (0.2 mmol) of cis-N-benzylazetidine-2,4-dicarboxylic acid benzyl methaneselenol ester, and 74.2 mg (0.22 mmol) of glycine benzyl ester tosylate in 1 ml of THF is added 84 μl (0.6 mmol) of triethylamine, followed by 45.2 mg (0.22 mmol) of cuprous bromidedimethylsulfide complex. After stirring for 2 h at room temperature, the suspension is diluted with methylene chloride, 2 g of (Si)$_2$ is added, and the whole is evaporated and chromatographed on SiO$_2$. EtOAc/hexanes (1:6) elutes 37.5 mg (46%) of the starting selenol ester cis-N-benzylazetidine-2,4-dicarboxylic acid benzyl methaneselenol ester, followed by 1.2 mg of cis-N-benzylazetidine-2,4-dicarboxylic acid dibenzyl ester. An unidentified impurity is eluted with EtOAc/hexanes (1:2), and finally the title compound with EtOAc/hexanes (2:1). Evaporation and drying in vacuo yields 25.0 mg (26%) of N-[cis-N-benzyl-4-(benzyloxycarbonyl)azetidine-2-carbonyl]glycine benzyl ester as a colorless syrup. $^1$H NMR (CDCl$_3$): δ7.72 (br. t, 1H, J=5.5), 7.4–7.2 (m, 15H), 5.17, 5.04 (narrow AB system, 2H), 3.97, 3.84 (AB system, 2H, J=18.5, both parts split into doublets with J=5.5), 3.78, 3.73 (AB system, 2H, overlapping), 3.80 (t, 1H, overlapping), 3.67 (t, 1H, J=8.5), 2.67 (dt, 1H, J=11(d), 8.5 (t)), 2.23 (dt, 1H, J=11 (d), 8 (t)). IR (neat): 3371, 3064, 3032, 2923, 2851, 1746, 1679, 1520, 1498, 1456, 1390, 1357, 1262, 1188, 1063, 1029, 741, 698 cm$^-$.

18 5 mg (39 μmol) of N-[cis-N-benzyl-4-(benzyloxycarbonyl)azetidine-2-carbonyl]glycine benzyl ester in 10 ml of methanol is hydrogenated in a Parr shaker over 34.5 mg of 20% Pd (OH)$_2$/C (containing 31% of water) under 4 atm of hydrogen for 4h. 5 ml of water is added, the catalyst is removed by filtration through a double paper filter and washed thoroughly with methanol/water (2:1), and the solution is evaporated. Filtration over SiO$_2$ (isopropanol/water/conc. ammonia 14:5:1), evaporation and drying in a vacuum desiccator over P$_2$O$_5$ and KOH affords 6.7 mg (85%) of N-(cis-4-carboxyazetidine-2-carbonyl)glycine as a colorless glass. $^1$H NMR (D₂O): δ 4.98 (t, 1H, J=8.5), 4.73 (T, 1H, overlapping), 3,86, 3,74 (AB system, 2H, J=17.5), 3.08 (dt, 1H, J=11.5 (d), 10 (t)), 2.55 (dt, 1H, J=12 (d), 8.5 (t)).

Mode of Preparation of the mono- and diamide of cis-Azetidine-2,4-dicarboxylic acid The following is a diagram for preparing mono- and diamide of cis-azetidine-2,4-dicarboxylic acid:

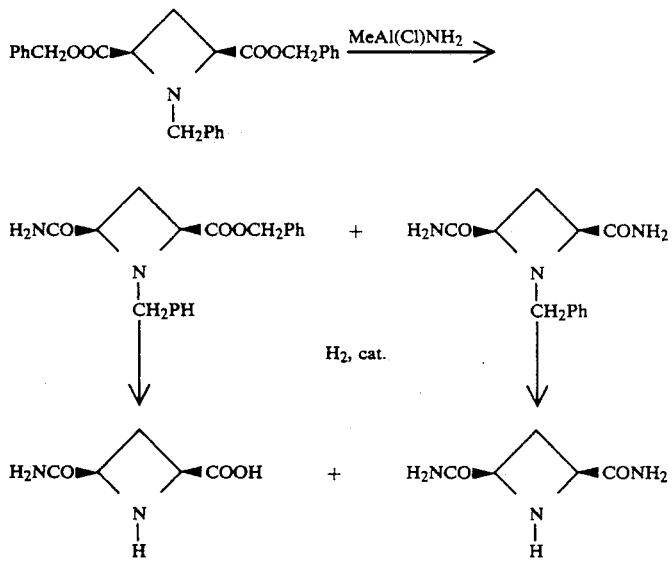

EXAMPLE 10

Preparation of cis-1-Benzyl-4-carbamoylazetidine-2-carboxylic acid benzyl ester and cis-1-Benzylazetidine-2,4-dicarboxamide.

To 108 mg (2 mmol) of finely powdered ammonium chloride is added, under a dry argon atmosphere via syringe at 0° C., 1 ml of trimethylaluminum (2M in toluene). After stirring at 0° C. for 20 minutes and at room temperature for 1 hour, a solution of 623 mg (1.5 mmol) of N-benzylazetidine-2,4-dicarboxylic acid dibenzyl ester (I) in 1 ml of toluene is added via syringe, and the mixture stirred at 50° C. for 2.5 hours. The mixture is then cooled in an ice bath, diluted with 10 ml of methylene chloride, and quenched by addition of 0.84 g (20 mmol) of NaF, followed by cautious dropwise addition of 0.36 ml (20 mmol) of water. After gas evolution has ceased, stirring is continued at room temperature for 20 minutes, and the fluoroaluminates are removed by suction filtration through a medium porosity sintered glass funnel and thoroughly washed with methylene chloride. Evaporation to a small volume and dilution with ethyl acetate/hexanes (1:5) causes precipitation of cis-N-benzylazetidine-2,4-dicarboxamide (III), which is collected on a sintered glass funnel and washed with the same solvent, to yield 80 mg (23%) of cis-N-benzylazetidine-2,4-dicarboxamide as a colorless solid. mp. 209°–212° C. (dec.) after filtration over SiO₂ (ethyl acetate/methanol 4:1). ¹NMR (CDCl₃): δ 7.4–7.25 (m, 5H), 6.29 (br. s, 2H), 5.30 (br. s, 2H), 3.76 (s, 2H), 3.72 (t, 2H, J=8.5), 2.89 (dt, 1H, J=9 (t), 11.5 (d)), 2.17 (dt, 1H, J=8.5 (t), 11.5 (d)). IR (nujol): 3474, 3409, 3318, 3156, 1673, 1647, 1570, 1418, 1323, 1291, 1148, 1005, 762, 708 cm⁻¹.

The mother liquid and washings are combined, evaporated, and chromatographed on silica gel to yield, in the sequence of elution, unreacted starting material (with ethyl acetate/hexanes 1:3; 22 mg, 43%), benzyl alcohol, and cis-1-benzyl-4-carbamoylazetidine-2-carboxylic acid benzyl ester (II) (with ethyl acetate), yielding 56 mg (11.5%) as a highly viscous film which partially solidifies on standing. ¹H NMR (CDCl₃): δ7.4–7.2 (m, 10H), 6.95 (br. s, 1H), 5.58 (br. s, 1H), 5.07 (s, 2H), 3.82, 3.71 (AB system, 2H, J=13), 3.80 (t, 1H, J=8.5), 3.61 (t, 1H, J=8.5), 2.70 (dt, 1H, J=8.5 (t), 11 (d)), 2.25 (dt, 1H, J=8 (t), 11 (d)). IR (neat): 3438, 3063, 3031, 2961, 2925, 2892, 1742, 1686, 1580, 1497, 1455, 1175, 1061, 1022, 747, 698 cm⁻¹.

EXAMPLE 11

Preparation of cis-4-Carbamoylazetidine-2-carboxylic acid 53 mg (163 μmol) of cis-1-benzyl-4-carbamoyl-azetidine-2-carboxylic acid benzyl ester (II) in 10 ml of methanol are hydrogenated in a Parr shaker over 18 mg of 10% Pd/C under a hydrogen pressure of 3.3 atm for 3 hours. 10 ml of water is added, the mixture filtered through a fluted filter, and the catalyst washed with several portions of methanol. Evaporation and drying in vacuo (0.1 torr, 4 hours) affords 22.6 mg (96%) of a colorless glass. ¹H NMR (D₂O): δ5.00 (t, 1H, J=9), 4.75 (t, 1H, J=9), 3.14 (dt, 1H, J=10 (t), 12 (d)), 2.52 (dt, 1H, J=8(t), 12 (d)). IR (nujol): 3399, 3141, 3019, 2537, 2409, 1688, 1615, 1563, 1391, 1294, 1217, 1165, 1115, 1048, 968, 887, 810, 762, 696, 637 cm⁻¹. Mass Spectra: EI: m/z 142(M-2H, 40%), 100 (100), 91 (14), 82 (27), 68 (28), 54 (50), 44 (95); CI (isobutane): m/z 145 (M+H, 100%), 126 (7), 100 (24), 99 (15), 84 (15), 72 (22).

EXAMPLE 12

Preparation of cis-Azetidine-2,4-dicarboxamide 45.8 mg (196 μmol) of cis-N-benzylazetidine-2,4-dicarboxamide in 10 ml of glacial acetic acid (no reaction occurs in methanol) are hydrogenated in a Parr shaker over 11 mg of 10% Pd/C under a hydrogen pressure of 4 atm for 7 hours. The mixture is filtered through a fluted filter and the catalyst washed with several portions of methanol. Evaporation and drying in vacuo yields a colorless film which crystallizes slowly on addition of a few drops of methanol. After standing in a freezer overnight, the crystals are isolated, washed with a small volume of ethyl acetate/methanol (5:1), and dried in vacuo; yield 16.7 mg (60%). Mp. 215°-218° C. (dec.) after strong shrinking and darkening from approx. 200° C. on (measured with oil bath preheated to 190° C). $^1$H NMR (D$_2$O): δ4.29 (t, 2H, J=8.5), 2.98 (dt, 1H, J=9 (t), 11 (d)), 2.23 (dt, 1H, J=8 (t), 11.5 (d)). IR (nujol): 3391, 3335, 3208, 3073, 1683, 1669, 1281, 1211, 1109, 1030, 843, 749, 722, 677 cm$^{-1}$. Mass Spectrum: CI(isobutane): m/z 144 (M+H, 100%), 99 (56).

Mode of Preparation of cis-Azetidine-2,3-dicarboxylic acid and its Diamide

The following is a diagram for preparing cis-azetidine-2,3-dicarboxylic acid and its diamide.

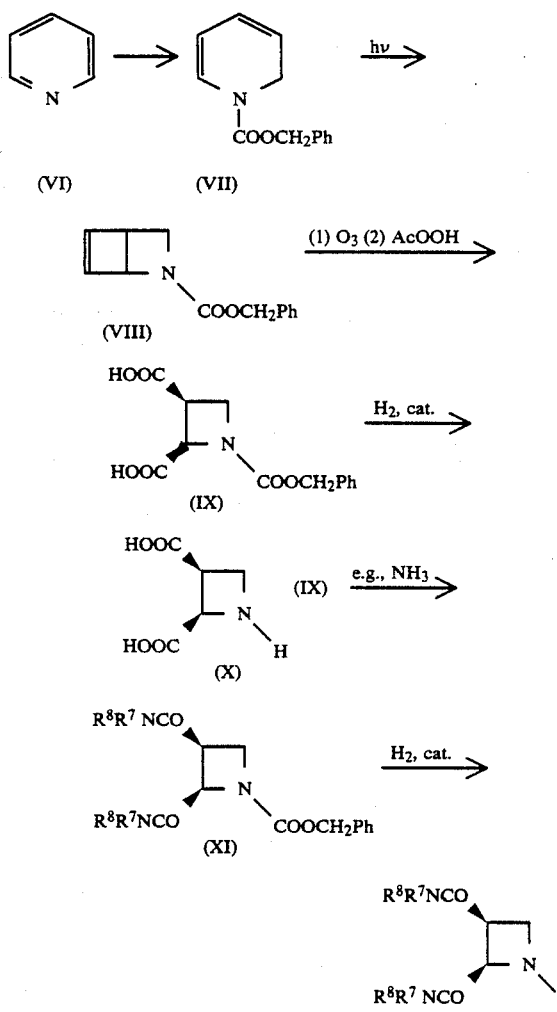

EXAMPLE 13

Preparation of cis-N-(Benzyloxycarbonyl)-azetidine-2,3-dicarboxylic acid;

A solution of pyridine (4.0 g., 0.050 mol) and NaBH$_4$ (1.0 g, 0.026 mol) in 20 ml of tetrahydrofuran is treated with benzyl chloroformate (8.5 g, 0.05 mol) over about 1 hour followed by stirring for 1.5 hour at −78° C. The mixture is added to ice-water and extracted with ether, and the extract is washed with 3% HCl solution and 3% NaOH solution. After the extract is dried and evaporated, 8.0 g of N-benzyloxycarbonyl-1,2-dihydropyridine is obtained in 74% yield. A 5% solution of N-benzyloxycarbonyl-1,2-dihydropyridine is then irradiated using a Rayonet photochemical reactor (RP-300 lamps) until the NMR spectrum shows consumption of the starting materials. The solvent is evaporated to give the crude product, N-(benzyloxycarbonyl)-2-azabicyclo[2.2.0]hex-5-ene (VIII). Pure (VIII) is obtained by passing the crude product through basic alumina with ether. (VIII) is then reacted with ozone in methanol at −78° C. followed by reaction with peroxyacetic acid to form cis-N-(benzyloxycarbonyl)-azetidine-2,3-dicarboxylic acid.

EXAMPLE 14

Preparation of cis-Azetidine-2,3-dicarboxylic acid cis-N-(Benzyloxycarbonyl)azetidine-2,3-dicarboxylic acid, 10% Pd/C and methanol are hydrogenated under 3 atm of hydrogen in a Parr shaker for 4 hours. The catalyst is filtered off and thoroughly washed. The solution is evaporated to dryness and dried in vacuo to arrive at cis-azetidine-2,3-dicarboxylic acid.

EXAMPLE 15

Preparation of cis-azetidine-2,3-dicarboxamide

A solution of cis-N-(benzyloxycarbonyl)azetidine-2,3dicarboxylic acid and, e.g., ammonia are reacted with [(CH$_3$)$_2$N]$_3$PCl$_2$ to form the cis-N-(benzyloxycarbonyl)azetidine-2,3-dicarboxamide (XI), as set forth by Appel et al., Chem. Ber. 116, 2037–2040 (1983). XI, 10% pd/C and methanol are hydrogenated in a Parr shaker under 3 atm of hydrogen, for 4 hours. The catalyst is filtered off and thoroughly washed. The solution is evaporated to dryness and dried in vacuo to arrive at cis-azetidine-2,3-dicarboxamide.

Preparation of the various ester derivatives of the cis-azetidine-2,3-dicarboxylic acids and N-substituted cis-azetidines can be accomplished by conventional esterification reactions utilizing lower alcohols and as per se known in the art or described hereinabove.

Mode of Preparation of cis-4-(Hydroxyalkyl)azetidine-2-carboxylic acid

The following is a diagram of the steps used in preparing cis-4-(hydroxyalkyl)azetidine-2-carboxylic acid derivatives

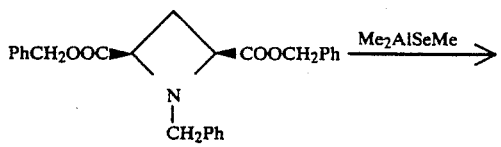

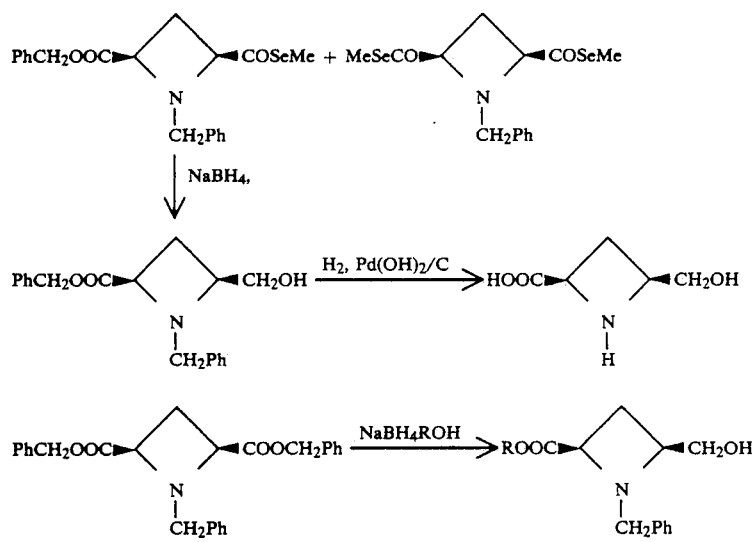

EXAMPLE 16

Preparation of N-Benzylazetidine-2,4-dicarboxylic acid benzyl methaneselenol ester, and N-Benzyl-azetidine-2,4-dicarboxylic acid bis(methaneselenol) ester 0.82 g (10.4 mmol) of selenium powder is dried at 140° C./0.1 torr for 1.5 h. Under an argon atmosphere, 5 ml (10 mmol) of trimethylaluminum (2M in toluene) is added, and the mixture is refluxed for 3h. After cooling and settling of the heterogeneous mixture, 3 ml of the supernatant solution is taken up in a syringe and added, with ice cooling and under argon to a solution of 1.66 g (4 mmol) of cis-N-benzylazetidine-2,4-dicarboxylic acid dibenzyl ester in 5 ml of dry ($P_2O_5$) methylene chloride. After 1.5 h at 0° C., TLC ($SiO_2$, EtOAc/hexanes 1:5) indicates the presence, in order of increasing polarity, of cis-N-benzylazetidine-2,4-dicarboxylic acid bis (methaneselenol) ester, cis-N-benzylazetidine-2,4-dicarboxylic acid benzyl methaneselenol ester, cis-N-benzylazetidine-2,4-dicarboxylic acid dibenzyl ester, and benzyl alcohol. The mixture is hydrolyzed cautiously at 0° C. by slow and dropwise addition of 2.5 ml of saturated aqueous sodium sulfate solution (vigorous methane evolution). Stirring is continued for 5 min. at r.t., sufficient $MgSO_4$ is added to bind the water and stirring continued for another 5 min. Solids are filtered off through a medium porosity sintered glass funnel and thoroughly washed with dry $CH_2Cl_2$. After evaporation, the residue is chromatographed on silica gel (EtOAc/hexanes 1:5) with application of slight pressure to ensure reasonably rapid elution of the hydrolytically sensitive selenol ester. There is obtained, in order of elution: (a) 0.28 g of a mixture of cis-N-benzylazetidine-2,4-dicarboxylic acid benzyl methaneselenol ester and cis-N-benzylazetidine-2,4-dicarboxylic acid bis (methaneselenol) ester, (b) 0.76 g (47%) of pure N-benzylazetidine-2,4-dicarboxylic acid benzyl methaneselenol ester; (c) 0.25 g (15%) of starting material cis-N-benzylazetidine-2,4-dicarboxylic acid dibenzyl ester, which can be recycled. cis-N-benzylazetidine-2,4-dicarboxylic acid benzyl methanselenol ester: viscous oil which solidifies on standing; mp. 56.5°–58° C. $^1H$ NMR ($CDCl_3$): δ7.37–7.20 (m, 10H), 4.97 (narrow AB system, 2H), 4.00, 3.70 (AB system, 2H, J=13), 3.80 (t, 1H, J=8}, 3.73 (t, 1H, J=8.5), 2.53 (dt, 1H, J=11 (d), 8.5 (t)), 2.32 (dt, 1H, J=11 (d), 7.5 (t)), 2.09 (s, 3H). IR (neat): 3063, 3031, 2930, 2882, 1744, 1694, 1495, 1455, 1271, 1215, 1169, 1055, 747, 696 cm$^{-1}$. cis-N-benzylazetidine-2,4-dicarboxylic acid bis (methaneselenol) ester: viscous oil which solidifies on standing; mp. 68.5°–71.5° C. $^1H$ NMR ($CDCl_3$): δ7.4–7.2 (m, 5H), 3.89 (s, 2H), 3.81 (t, 2H, J=8), 2.57 (dt, 1H, J=11 (d), 8.5 (t)), 2.11 (dt, 1H, overlapping), 2.10 (s, 6H). IR (neat): 3063, 3029, 2930, 2870, 1694, 1495, 1269, 1161, 1123, 1026, 866, 762, 710 cm$^{-1}$.

EXAMPLE 17

Preparation of N-Benzyl-4-(hydroxymethyl)-azetidine-2-carboxylic acid benzyl ester 324 mg (0.8 mmol) of cis-N-benzylazetidine-2,4-dicarboxylic acid benzyl methaneselenol ester is dissolved in 2 ml of methylene chloride and diluted with 30 ml of absolute ethanol. 3 portions of 91 mg (2.4 mmol) each of $NaBH_4$ are added at 0° C. in intervals of 20 min., and stirring at 0° C. is continued for another 40 min. The mixture is hydrolyzed by cautious addition of 1 ml of acetic acid (vigorous hydrogen evolution). 6 g of silica gel is added, the solvent evaporated, and the residue placed on top of a $SiO_2$ column. A small amount of benzyl alcohol formed as a byproduct is first eluted with EtOAc/hexanes (1:2), and then N-benzyl-4-(hydroxymethyl)azetidine-2-carboxylic acid benzyl ester is eluted with EtOAc/hexanes (1:1). 179 mg (72%) of a colorless oil is obtained. $^1H$ NMR ($CDCl_3$): δ7.37–7.25 (m, 10H), 5.09 (s, 2H), 3.86, 3.65 (AB system, 2H, J=12.5), 3.73 (t, 1H, J=8.5), 3.39 (tt, 1H, J=8, 2.5) 3.24–3.13 (m, 2H), 2.58 (br. dd, J=11.5, 2), 2.35 (dt, 1H, J=11 (d), 8 (t)), 2.27 (dt, 1H, J=11 (d), 8 (t)). IR (neat): 3401, 3065, 3031, 2924, 2872, 1742, 1613, 1497, 1455, 1395, 1216, 1177, 1094, 1028, 749, 698 cm$^{-1}$. MS m/z 311 (M+, 0.1%), 309 (0.2), 294 (0.3), 293 (0.2), 280 (33), 176 ((26), 91 (100). $C_{19}H_{20}NO_2$ (M+–OH) calcd. 294.1494, found 294.1495.

EXAMPLE 18

Preparation of 4-(Hydroxymethyl)azetidine-2-carboxylic acid 179 mg (0.575 mmol) of N-benzyl-4-(hydroxymethyl)azetidine-2-carboxylic acid benzyl ester and 60 mg of 20% Pd(OH)$_2$/C (containing 31% of water) in 30 ml of methanol are hydrogenated in a Parr shaker under 4 atm of hydrogen for 3.5 h. The catalyst is filtered off through a double paper filter and washed with methanol, the solution evaporated, and the residue chromatographed on silica gel (isopropanol/water/conc. NH$_3$ 14:5:1) to yield, after evaporation and drying i.v., 53.6 mg (71%) of 4-(hydroxymethyl)azetidine-2-carboxylic acid as a colorless solid. $^1$H NMR (D$_2$O): δ 4.71 (t, 1H, J=9), 4.56 (m, 1H), 3.80 (m, 2H), 2.81 (dt, 1H, J=12 (d), 9.5 (t)), 2.43 (dt, 1H, J=12.5 (d), 8.5 (t)). IR (nujol): 3239, 3146, 2589, 2438, 1620, 1565, 1410, 1327, 1302, 1188, 1099, 1038, 999, 885, 828, 758, 725 cm$^{-1}$.

EXAMPLE 19

Preparation of N-Benzyl-4-(hydroxymethyl)-azetidine-2-carboxylic acid ethyl ester This compound is obtained, as the result of a concomitant transesterification, when NaBH$_4$ reduction is applied directly to cis-N-benzylazetidine-2,4-dicarboxylic acid dibenzyl ester. To 104 mg (0.25 mmol) of cis-N-benzylazetidine-2,4-dicarboxylic acid dibenzyl ester in 2.5 ml of absolute ethanol is added, at r.t. in small portions over a period of 1 h, 45 mg (1.25 mmol) of NaBH$_4$. Quenching with 50 μl of acetic acid is followed by filtration through a medium porosity sintered glass funnel, repeated washing of the solids with methylene chloride, and evaporation. The residue is chromatographed on SiO$_2$; EtOAc/hexanes (1:3) elutes benzyl alcohol, EtOAc/hexanes (1:1) the product. The product is a colorless oil obtained in 39.8 mg (64%) yield. $^1$H NMR (CDCl$_3$): δ7.35–7.25 (m, 5H), 4.09 (q, 2H, J=7), 3.84, 3.67 (AB system, 2H, J=12.5), 3.66 (t, 1H, J=8.5), 3.38 (tt, 1H, J=8, 2.5), 3.25-3.15 (m, 2H), 2.81 (br., 1H), 2.37-2.21 (m, 2H), 1.20 (t, 3H, J=7). IR (neat): 3432, 3063, 2928, 2870, 1736, 1495, 1455, 1194, 1096, 1034, 961, 739, 704 cm$^{-1}$.

Preparation of cis-4-(Dialkoxymethyl)azetidine-2-carboxylic acid

The following is a flow diagram of preparing the cis-4-(dialkoxymethyl)azetidine-2-carboxylic acid derivatives.

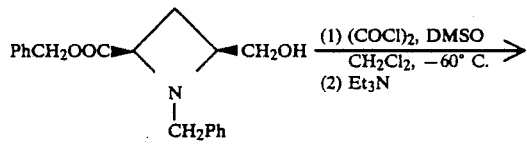

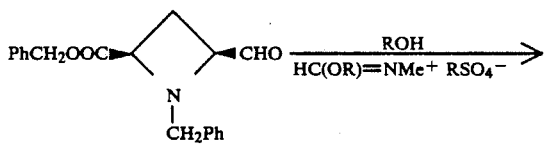

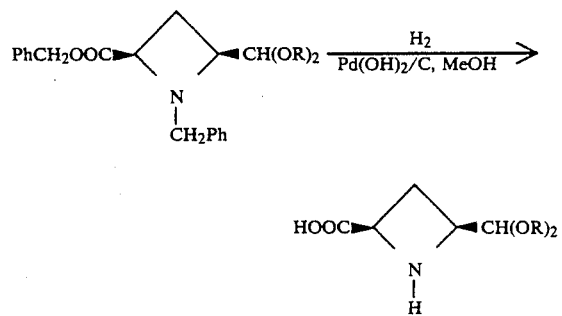

EXAMPLE 20

Preparation of cis-4-(Dimethyoxymethyl)azetidine-2-carboxylic acid

To 64 μl (0.73 mmol) of oxalyl chloride in 1 ml of methylene chloride is added, dropwise at −60° C., 106 μl (1.5 mmol) of dimethyl sulfoxide in 0.5 ml of methylene chloride. After stirring at −60° C. for 5 min., 45.7 mg (147 μmol) of cis-N-benzyl-4-(hydroxymethyl)azetidine-2-carboxylic acid benzyl ester in 0.7 ml of methylene chloride is added dropwise, and the mixture is stirred at −60° C. for 30 min. 0.63 ml (4.5 mmol) of triethylamine is added, and after another 10 min. at −60° C. the mixture is quenched with water. Aqueous workup (sat. aq. NaHC)$_3$/methylene chloride), drying over MgSO$_4$, evaporation, and filtration over SiO$_2$ (EtOAc/hexanes 1:1) afford 41.6 mg of the very impure crude product cis-N-benzyl-4-formylazetidine-2-carboxylic acid benzyl ester, which is difficult to purify in quantity, but can be used as such in the following step.

An analytical sample is obtained by HPLC (2 Waters 501 HPLC pumps with automated gradient controller and model 441 absorbance detector operating at 254 nm; Waters Millipore ® 24×1 cm μPorasil TM column; EtOAc/hexanes 35:65, 5 ml/min., retention time 4.8 min.) as a colorless oil. $^1$H NMR (CDCl$_3$): δ 9.24(d,1H,J=3), 7.40–7.18 (m,10 H), 5.16 (s,2H), 4.07, 3.57 (AB system, 2H, J=12.5), 3.84 (t, 1H, J=8.5), 3.50 (dt, 1H, J=3(d), 8.5 (t)), 2.49–2.34 (m,2H). IR (neat): 3063, 3031, 2886, 1743, 1732, 1497, 1455, 1354, 1267, 1175, 1055, 750, 698 cm$^{-1}$. MS (EI): m/z 280 (M—CHO, 31%), 91 (91%), 57 (100%); (CI, isobutane): m/z 310 (M+H, 100%), 280 (32%), 91 (35%).

28 μl (0.36 mmol) of dimethylformamide and 34 μl (0.36 mmol) of dimethyl sulfate are stirred for 2 h in a screw-capped vial at 80°–85° C. After cooling, 16 μl (0.4 mmol) of methanol is added, followed by 37.5 mg (121 μmol) of the above crude aldehyde, cis-N-benzyl-4-formylazetidine-2-carboxylic acid benzyl ester. This mixture is stirred at room temperature for 5 h and then chromatographed on SiO$_2$ (previously treated with 10 weight% of conc. aq. ammonia; EtOAc/hexanes 1:6). After elution of a forerun and evaporation, 15.5 mg (30% from the alcohol) of cis-N-benzyl-4-(dimethoxymethyl)azetidine-2-carboxylic acid benzyl ester is obtained as a colorless oil. $^1$H NMR (CDCl$_3$): δ7.4–7.2(m, 10 H), 5.04, 4.96 (AB system, 2H, J=12.5), 4.27 (d, 1H, J=6.5), 3.90, 3.70 (AB system, 2H, J=13), 3.59 (t, 1H, J=8.5), 3.36 (s, 3H), 3.35 (s, 3H), 3.25 (dt, 1H, J=6.5 (d), 8 (t)), 2.19 (t, 2H, J=8).

12.5 mg (35 μmol) of cis-N-benzyl-4-(dimethoxymethyl)azetidine-2-carboxylic acid benzyl ester in 10 ml of methanol is hydrogenated in a Parr shaker over 53 mg of 20% Pd(OH)$_2$/C (containing 31% water) under 4 atm of hydrogen for 3 h. Filtration through a double paper filter, repeated washing with methanol and evaporation gives a crude product which is filtered over silica gel with isopropanol/water/conc. ammonia (17:2:1) to yield 3.0 mg (49%) of cis-4-(dimethoxymethyl)azetidine-2-carboxylic acid as a colorless glass. $^1$H NMR (D20): δ4.73 (d, 1H, overlapping), 4.72 (t, 1H, overlapping), 3.53 (s, 3H), 3.50 (s, 3H), 2.80 (dt, 1H, J=12 (d), 9.5(t)), 2.50 (dt, 1H, J=12(d), 8(t)).

IN VITRO AND IN VIVO STUDIES

For ease of discussing and reporting the biological data, the following abbreviations have been devised for representative compounds of the present invention.

Az1 cis-azetidine-2,4-dicarboxylic acid t-butyl methyl ester
Az2 trans-azetidine-2,4-dicarboxylic acid-t-butyl methylester
Az3 cis-azetidine-2,4-dicarboxylic acid mono-t-butyl ester
Az4 trans-azetidine-2,4-dicarboxylic acid mono-t-butyl ester
Az5 cis-azetidine-2,4-dicarboxylic acid
Az6 trans-azetidine-2,4-dicarboxylic acid
Az7 cis-azetidine-2,4-dicarboxylic acid dimethyl ester
Az8 cis-4-carbamoylazetidine-2-carboxylic acid
Az9 cis-azetidine-2,4-dicarboxamide
Az10 cis-N-benzylazetidine-2,4-dicarboxylic acid
Az11 cis-azetidine-2,4-dicarboxylic acid methyl ester
Az12 L-2-azetidinecarboxylic acid (known)
Az13 cis-4-(hydroxymethyl)azetidine-2-carboxylic acid
Az18 cis-azetidine-2,4-dicarboxylic acid, di-tert.butyl ester

EXAMPLE 21

Characterization of the experimental model

Studies described hereinbelow on the usefulness of the compounds were performed on primary cultures of cerebellar granule cells prepared from 8-day old rats according to the procedures as set forth in Wroblewski et al., Neuropharmacology 24(9), 919–921 (1985). These cultures are characterized by the presence of four subtypes of excitatory amino acid receptors, classified on the basis of the coupling of their recognition sites to specific signal transduction systems, as well as according to the pharmacology of their recognition sites. The classification distinguishes between excitatory amino acid recognition sites coupled with PI hydrolysis ($G_p$) and those coupled with the activation of Ca$^{2+}$ influx ($G_C$). This is disclosed in greater detail in Wroblewski et al. Proc. Natl. Acad. Sci. USA 184(14), 5068–5072 (1987). $G_{P1}$ and $G_{C1}$ receptors are activated by glutamate (GLU), aspartate (ASP), N-methyl-D-aspartate (NMDA), are antagonized by 2-amino-5-phosphonovalerate (APV), and inhibited by Mg$^{2+}$. These two receptor subtypes correspond to the NMDA receptor, however, two distinct receptors must be postulated on the basis of their signal transducing mechanisms. The $G_{P2}$ receptor is activated by glutamate and quisqualate (QUIS), and is insensitive to Mg$^{2+}$ and APV. The $G_{C2}$ receptor is activated by kainate (KAIN) and preferentially antagonized by cis-piperidine-2,3-dicarboxylate. The $G_{C2}$ receptor is also insensitive to Mg$^{2+}$ inhibition. These two receptors correspond to the quisqualate and kainate receptors, respectively.

20 μM solutions of NMDA, GLU, ASP, QUIS, and KAIN are prepared by dissolving the respective quantities of NMDA, GLU, ASP, QUIS, and KAIN into normal saline and are administered icv to determine the degree of potentiation of calcium influx by cis-azetidine-2,4-dicarboxylic acid.

Cis-azetidine-2,4-dicarboxylic acid and derivatives selectively potentiate signal transduction at the $G_{C1}$ and $G_{P1}$ receptors. Referring to Table 1 the influx of calcium stimulated by NMDA, GLU, ASP and QUIS acting at the $G_{C1}$ receptor is potentiated by cis-azetidine-2,4-dicarboxylic acid, while the action of KAIN at the $G_{C2}$ receptor is not affected.

TABLE 1

Cis-azetidine-2,4-dicarboxylic acid potentiates calcium influx stimulated by excitatory amino acid receptor agonists

| Agonist 20 μM/Normal Saline | Percent Activity |
|---|---|
| NMDA | 188 |
| Glutamate (GLU) | 169 |
| Aspartate (ASP) | 144 |
| Quisqualate (QUIS) | 124 |
| Kainate (KAIN) | 104 |

EXAMPLE 22

Stereoselectivity of the action of azetidines

50 μM solutions of Az1, Az2, Az3, Az4, Az5, and Az6 are prepared by dissolving the appropriate quantity of Az1, Az2, Az3, Az4 and Az5 into normal saline. The respective solutions are then administered icv to determine the effect on calcium influx and PI hydrolysis. The results are reported in Table 2.

TABLE 2

Action of cis and trans stereoisomers of azetidines on calcium influx and PI hydrolysis stimulated by excitatory amino acids

| Azetidine hydrolysis 50 μM in Normal Saline | Calcium Influx % of stimulation by 10 μM GLU | PI 20 μM GLU |
|---|---|---|
| Az1 (cis) | 107 | 117 |
| Az2 (trans) | 104 | — |
| Az3 (cis) | 141 | 125 |
| Az4 (trans) | 100 | 109 |
| Az5 (cis) | 207 | 124 |
| Az6 (trans) | 103 | 83* |

As disclosed above, the cis isomers are particularly more active than the trans. *This value shows antagonistic activity.

EXAMPLE 23

Structure-activity relationships

50 μM solutions of Az1, Az3, Az5, Az7, Az11, Az8, Az9, Az12, Az10 and Az13 are prepared by dissolving the appropriate quantity of above mentioned azetidines into Normal Saline. The compounds are then administered icv. The potentiation of calcium influx of the above identified azetidines is reported in Table 3.

TABLE 3

Potentiation of calcium influx by cis-azetidines

| Azetidine 50 μM in Normal Saline | Group 1 | Group 2 | agonist | % activity |
|---|---|---|---|---|
| Az1 | t-butyl ester | methyl ester | Glu 10 μM | 107 |
| Az3 | t-butyl ester | acid | Glu 10 μM | 141 |
|  |  |  | Glu 20 μM | 136 |
| Az5 | acid | acid | Asp 10 μM | 196 |

TABLE 3-continued

| Potentiation of calcium influx by cis-azetidines | | | | |
|---|---|---|---|---|
| Azetidine 50 μM in Normal Saline | Group 1 | Group 2 | agonist | % activity |
| | | | Asp 20 μM | 141 |
| | | | Glu 10 μM | 207 |
| | | | Glu 20 μM | 157 |
| Az7 | methyl ester | methyl ester | Glu 50 μM | 68 |
| Az11 | methyl ester | acid | Glu 10 μM | 122 |
| Az8 | acid | amide | Asp 20 μM | 150 |
| Az9 | amide | amide | Asp 20 μM | 106 |
| Az12 | acid | H | Glu 20 μM | 110 |
| Az10 | (N-benzyl) acid | acid | Asp 10 μM | 121 |
| Az13 | alcohol | acid | Asp 10 μM | 159 |

EXAMPLE 24

Concentration of cGMP in mouse cerebellum after the peripheral administration of cis-azetidine dicarboxylic acid di-tert.butyl ester cis-Azetidine-2,4-dicarboxylic acid di-tert.butyl ester (Az18) is administered to mice at a dose of 100 mg/kg body weight in Normal Saline. The mice are sacrificed at 1 and 15 minutes after injection by microwave irradiation. The results on the concentration of cGMP (mean±SEM) are reported in Table 4.

TABLE 4

| Compound 100 mg/kg | (mean ± SEM) | Number of mice |
|---|---|---|
| Az18 - 1 min. | 8.50 ± 0.84 | 6 |
| Az18 - 15 min. | 1.67 ± 0.17 | 4 |

While not being bound to any theory, the cis-azetidines and derivatives thereof are believed to act by increasing the potency but not the efficacy of GLU action at the $G_{Cl}$ receptor.

EXAMPLE 25

Inhibition of Phencyclidine Action by cis-Azetidines

Phencyclidine (PCP), once used as an anaesthetic, produces strong psychotropic effects manifested in humans by a state of sensory isolation, hallucinations and confusional states. It is one of the most widely abused drugs in the United States. One of the possible mechanisms of action of PCP involves the noncompetitive inhibition of the signal transduction at excitatory amino acid receptors through allosteric interaction at a site distinct from the primary transmitter site, (see Proc. Natl. Acad. Sci. USA discussed above). However, cis-azetidine-2,4-dicarboxylic acid exhibits the ability to decrease the action of PCP on ASP-stimulated signal transduction as shown in Table 5. This action occurs at a site different than the binding site for PCP, since cis-azetidine-2,4-dicarboxylic acid failed to displace the specific binding of [$^3$H]PCP in radioligand binding studies.

TABLE 5 cis-azetidine-2,4-dicarboxylic acid prevents the inhibition of ASP-stimulated calcium influx by Phencyclidine
Concentration nmol $^{45}Ca^{2+}$/mg protein

| | ASP 50 μM | + | ASP 50 μM Az5 50 μM in Normal Saline |
|---|---|---|---|
| No PCP | 31.3 ± 3.4 | | 64.5 ± 2.6 |
| PCP 20 nM | 23.0 ± 1.7 | | 57.2 ± 3.2 |
| PCP 50 nM | 9.2 ± 0.5 | | 32.2 ± 1.3 |
| PCP 100 nM | 0.7 ± 0.1 | | 13.3 ± 0.3 |

Azetidines increase the potency but not the efficacy of GLU action at the $G_{Cl}$ receptor. When calcium influx stimulated by GLU is measured in the absence and presence of Az5, the $EC_{50}$ for GLU is decreased by 50 μM Az5 from 51 μM to 7 μM. This indicates a 7-fold potentiation of the action of GLU.

These data suggest that cis-azetidines may interact with a specific recognition site different from the GLU recognition site but located within the same receptor complex. This interaction results in the potentiation of the action of the primary transmitter (GLU or ASP). Since cis-azetidines are inactive in the absence of the primary transmitter, they serve a modulatory function. It is possible that cis-azetidines interact with a positive allosteric modulatory site of the glutamatergic receptors.

EXAMPLE 26

IN VIVO STUDIES

Characterization of the in vivo model

The action of the NMDA receptor subtype can be estimated in vivo by measuring the changes in the content of cyclic GMP (cGMP) in the rat cerebellum after intracerebroventricular (icv) injections of NMDA. The increases in cGMP content induced by NMDA are antagonized by APV indicating receptor selectivity. In terms of its pharmacology and of its mechanism of signal transduction the active receptor in the above conditions can be compared to the $G_{Cl}$ receptor measured in cultures of cerebellar granule cells. See Novelli et al., J. Neuroscience 7(1), 40–47 (1987) for a more detailed explanation of the procedure.

EXAMPLE 27

Action of the cis-azetidine derivatives in vivo

In two series of experiments rats are injected icv with NMDA together with or without cis-azetidine-2,4-dicarboxylic acid. The results of the measurements of cGMP content in the cerebellum are shown in Table 6.

TABLE 6

| TIME 10 min | | | TIME 5 min | | |
|---|---|---|---|---|---|
| Injection | cGMP | % Control | Injection | cGMP | % Control |
| Saline | 7.8 + 1.9 | 100 | Saline | 4.8 + 0.8 | 100 |
| NMDA 1 μg | 10.5 + 2.3 | 135 | NMDA 2 μg | 5.6 + 0.8 | 136 |
| Az5 10 μg | 14.9 + 1.3 | 192 | AZ5 2 μg | 6.8 + 0.8 | 142 |
| NMDA + Az5 | 16.5 + 2.8 | 211 | NMDA + Az5 | 16.1 + 2.9 | 334 |

In both series of experiments cis-azetidine-2,4-dicarboxylic acid potentiated the action of the endogenous receptor agonist as well as the action of injected NMDA.

The compounds of the present invention may be made into pharmaceutical compositions by combination with appropriate medical carriers or diluents, and may be formulated into preparations in solid, semisolid, liquid or gaseous form such as tablets, capsules, powders, granules, ointments, solutions, suppositories, injections, inhalants, aerosols in usual ways for oral or parenteral administration. The following methods and excipients are merely exemplary and are in no way limiting.

In pharmaceutical dosage forms, the compounds of the present invention may be used in the form of their pharmaceutically acceptable salts, and also may be used alone or in appropriate association, as well as in combination with other pharmaceutically active compounds.

In the case of oral preparations, the compounds may be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

Furthermore, they may be made into suppositories by mixing with a variety of bases such as emulsifying bases or water-soluble bases.

The compounds of the present invention may be formulated into preparations for injections by dissolving, suspending or emulsifying them in aqueous solvents such as normal saline, Dextrose 5%, or non-aqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In case of inhalations or aerosol preparations, the compounds of the invention in the form of a liquid or minute powder may be filled up in an aerosol container with gas or liquid spraying agents, and if desired, with conventional adjuvants such as humidifying agents added. They may also be applied as pharmaceuticals for non-pressurized preparation such as in a nebulizer or an atomizer.

The desirable dose of the azetidine derivatives of the present invention varies with the subject, drug form, method and period of administration. However, in order to obtain desirable effects, generally it is recommended to administer 0.1 mg to 100 mg/kg body weight of the compounds of the present invention. In terms of composition, compounds should be present between 0.1 to 100% by weight.

We claim:

1. A method of treating memory disorders or learning disorders in a mammal which comprises administering to said mammal a therapeutically effective amount of a compound having the formula:

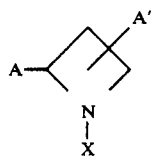

wherein A and A' are the same or different and selected from the group consisting of

and wherein R and R' are the same or different and selected from the group consisting of hydrogen, lower alkyl, benzyl, and an amino acid; n=1-6; X is hydrogen, an acyl group or a benzyl group; or a pharmaceutically acceptable salt thereof.

2. A method according to claim 1, which comprises administering a therapeutically effective amount of a compound having the formula:

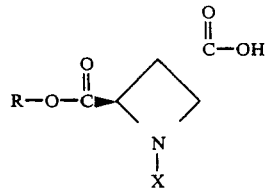

wherein R is selected from the group consisting of hydrogen and lower alkyl, and X is hydrogen; or a pharmaceutically acceptable salt thereof.

3. A method according to claim 1, which comprises administering a therapeutically effective amount of a compound having the formula:

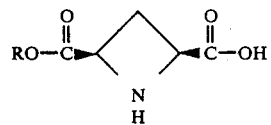

wherein R is a lower alkyl; or a pharmaceutically acceptable salt thereof.

4. A method according to claim 1, which comprises administering a therapeutically effective amount of a compound having the formula:

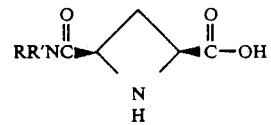

wherein R and R' are the same or different and are lower alkyl or hydrogen; or a pharmaceutically acceptable salt thereof.

5. A method according to claim 1, which comprises administering a therapeutically effective amount of a compound having the formula:

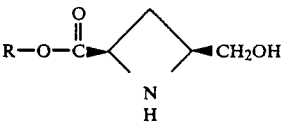

wherein R is a hydrogen or a lower alkyl group; or a pharmaceutically acceptable salt thereof.

6. A method according to claim 1, which comprises administering a therapeutically effective amount of a compound having the formula:

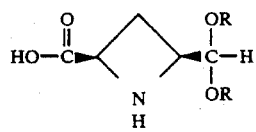
wherein R is a lower alkyl group; or a pharmaceutically acceptable salt thereof.
* * * * *
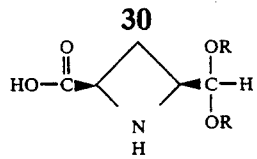
wherein R is a lower alkyl group; or a pharmaceutically acceptable salt thereof.
* * * * *